(12) United States Patent
Konishi et al.

(10) Patent No.: US 9,023,654 B2
(45) Date of Patent: May 5, 2015

(54) METHOD AND APPARATUS FOR MEASURING BROMATE IONS

(71) Applicant: Metawater Co., Ltd., Tokyo (JP)

(72) Inventors: Natsumi Konishi, Tokyo (JP); Eri Hasegawa, Tokyo (JP); Yoshiharu Tanaka, Tokyo (JP); Shukuro Igarashi, Hitachi (JP); Takao Ohtomo, Hitachi (JP)

(73) Assignee: Metawater Co., Ltd., Chiyoda-Ku (JP)

( * ) Notice: Subject to any disclaimer, the term of this patent is extended or adjusted under 35 U.S.C. 154(b) by 0 days.

(21) Appl. No.: 14/146,073

(22) Filed: Jan. 2, 2014

(65) Prior Publication Data

US 2014/0113381 A1    Apr. 24, 2014

Related U.S. Application Data

(63) Continuation of application No. PCT/JP2012/068014, filed on Jul. 13, 2012.

(30) Foreign Application Priority Data

Jul. 25, 2011  (JP) .................... 2011-162170

(51) Int. Cl.
*G01N 21/64* (2006.01)
*G01N 21/77* (2006.01)
*G01N 31/22* (2006.01)
*G01N 21/27* (2006.01)

(52) U.S. Cl.
CPC ............... *G01N 31/22* (2013.01); *G01N 21/64* (2013.01); *G01N 21/6428* (2013.01); *G01N 21/274* (2013.01); *G01N 21/643* (2013.01); *G01N 21/77* (2013.01); *G01N 2021/6419* (2013.01); *G01N 2021/6439* (2013.01); *G01N 2021/7786* (2013.01)

(58) Field of Classification Search
CPC ..... G01N 31/22; G01N 31/00; G01N 21/643; G01N 21/64; G01N 21/77; G01N 21/274
USPC .............. 436/133; 422/82.08, 82.05, 68.1, 50
See application file for complete search history.

(56) References Cited

U.S. PATENT DOCUMENTS

2010/0330694 A1    12/2010    Igarashi et al.

FOREIGN PATENT DOCUMENTS

JP    09-119925 A1    5/1997
JP    2006-022339 A1    1/2006
WO    2009/116554 A1    9/2009

OTHER PUBLICATIONS

International Search Report and Written Opinion (Application No. PCT/JP2012/068014) dated Aug. 14, 2012.

*Primary Examiner* — Christine T Mui
(74) *Attorney, Agent, or Firm* — Burr & Brown, PLLC

(57) ABSTRACT

A method for measuring bromate ions includes: an adding step of adding a fluorescent substance whose fluorescence intensity changes by the coexistence of bromate ions to sample water; a measuring step of measuring the fluorescence intensity of the fluorescent substance; a difference calculating step of calculating a difference between the fluorescence intensity measured and a reference fluorescence intensity of reference sample water that contains no bromate ion; and a concentration calculating step of calculating bromate ion concentration from the calculated fluorescence intensity difference. The measuring step includes a step of measuring the fluorescence intensity at any one of a case where an excitation wavelength is 264 nm and an emission wavelength is 400 nm, a case where the excitation wavelength is 264 nm and the emission wavelength is 480 nm, and a case where the excitation wavelength is 300 nm and the emission wavelength is 400 nm.

2 Claims, 7 Drawing Sheets

METHOD AND APPARATUS FOR MEASURING BROMATE IONS

CROSS-REFERENCE TO RELATED APPLICATIONS

This application is a continuation of PCT International Application No. PCT/JP2012/068014 filed on Jul. 13, 2012 which claims the benefit of priority from Japanese Patent Application No. 2011-162170 filed on Jul. 25, 2011, the entire contents of which are incorporated herein by reference.

BACKGROUND OF THE INVENTION

1. Field of the Invention

The present invention relates to a method and an apparatus for measuring bromate ions, more specifically for measuring bromate ion concentration in sample water.

2. Description of the Related Art

Raw city water such as river water contains bromide ions ($Br^-$). Upon performing ozonation on the raw city water, the bromide ions react with ozone to produce bromate ions ($BrO_3^-$). Bromate ions are considered to be a carcinogenic substance. In view of this, the World Health Organization (WHO) sets the guideline value for bromate ion concentration in drinking water to be 10 μg/L. The Japanese government revised the ministerial ordinance on the water quality criteria published on May 30, 2003 to set the standard value of bromate ion concentration in city water to be 10 μg/L.

Ion chromatograph-post-column absorptiometry (the IC-PC method) has been known as a method for measuring bromate ion concentration in water. The IC-PC method is a method for quantifying bromate ions by separating bromate ions in sample water using an anion-exchange column, adding sulfuric acid and a mixed solution of sodium nitrite and sodium bromide to an eluate of the bromate ions, thereby converting the bromate ions into tribromide ions, and measuring the ultraviolet absorbance of the tribromide ions. In this IC-PC method, a two-step reaction occurs, requiring that the first-step reaction convert bromic acid into tribromide ions with a potassium bromide/sulfuric acid and the second-step reaction ensure the linearity of a calibration Line in the low-concentration range using a sodium nitrite solution. Given this situation, the measurement operation for the bromate ion concentration by the IC-PC method is complicated and is hence hard to be adapted to process equipment.

In view of such a background, developed recently is a method for measuring bromate ion concentration using fluorescence intensity. In this method, trifluoroperazine (TFP), which is a fluorescent substance that reacts upon coexistence with bromate ions, and hydrochloric acid are added to sample water, its fluorescence intensity is measured at an excitation wavelength of 300 nm and an emission wavelength of 480 nm, and a fluorescence intensity difference with a reference sample that contains no bromate ion is calculated. Using a calibration line between fluorescence intensity difference and bromate ion concentration, bromate ion concentration is measured from the calculated fluorescence intensity difference. This method can measure bromate ions simply, quickly, and with high precision.

TFP exhibits a quenching reaction when the excitation wavelength and the measurement emission wavelength are 300 nm and 480 nm, respectively. However, when the excitation wavelength is 300 nm and the measurement emission wavelength is 480 nm, the optimum hydrochloric acid concentration that ensures the linearity of a calibration line is as extremely high as 6 N. In a conventional method, because the hydrochloric acid concentration for use in measurement is high, equipment is likely to corrode, and running costs increase. In this measurement condition, bromate ion concentration may not be measured accurately because the slope of the calibration line changes due to coexisting nitrate ions. In view of such a background, anticipated is a technology that can measure bromate ion concentration with high precision without being affected by the coexisting substance while reducing hydrochloric acid concentration required for measurement.

For the foregoing reasons, there is a need for a method and an apparatus for measuring bromate ions that can measure bromate ion concentration with high precision while reducing hydrochloric acid concentration required for measurement.

SUMMARY OF THE INVENTION

According to one aspect of the present invention, a method for measuring bromate ions includes: an adding step of adding a fluorescent substance whose fluorescence intensity changes by coexistence of bromate ions to sample water and further adding hydrochloric acid to a sample mixture of the sample water with the fluorescence substance so that the sample mixture becomes an acidic condition; a measuring step of measuring the fluorescence intensity of the fluorescent substance; a difference calculating step of calculating a difference between the fluorescence intensity measured at the measuring step and a reference fluorescence intensity of reference sample water that contains no bromate ion as a fluorescence intensity difference; and a concentration calculating step of calculating bromate ion concentration from the fluorescence intensity difference calculated at the difference calculating step using a pre-determined calibration line between fluorescence intensity difference and bromate ion concentration, wherein the measuring step includes a step of measuring the fluorescence intensity at any one of cases where, (a) an excitation wavelength is 264 nm and an emission wavelength is 400 nm, (b) the excitation wavelength is 264 nm and the emission wavelength is 480 nm, and (c) the excitation wavelength is 300 nm and the emission wavelength is 400 nm.

According to another aspect of the present invention, an apparatus for measuring bromate ions, includes: an adding unit that adds a fluorescent substance whose fluorescence intensity changes by coexistence of bromate ions to sample water and further adds hydrochloric acid to a sample mixture of the sample water with the fluorescence substance so that the sample mixture becomes an acidic condition; a measuring unit that measures the fluorescence intensity of the fluorescent substance; a difference calculating unit that calculates a difference between the fluorescence intensity measured by the measuring unit and a reference fluorescence intensity of reference sample water that contains no bromate ion as a fluorescence intensity difference; and a concentration calculating unit that calculates bromate ion concentration from the fluorescence intensity difference calculated by the difference calculating unit using a pre-determined calibration line between fluorescence intensity difference and bromate ion concentration, wherein the measuring unit that measures the fluorescence intensity measures the fluorescence intensity at any one of cases where, (a) an excitation wavelength is 264 nm and an emission wavelength is 400 nm, (b) the excitation wavelength is 264 nm and the emission wavelength is 480 nm, and (c) the excitation wavelength is 300 nm and the emission wavelength is 400 nm.

The above and other features, advantages and technical and industrial significance of this invention will be better understood by reading the following detailed description of presently preferred embodiments of the invention, when considered in connection with the accompanying drawings.

DETAILED DESCRIPTION OF THE INVENTION

A method for measuring bromate ions as an embodiment of the present invention is described below with reference to the accompanying drawings.

Figure 1A:
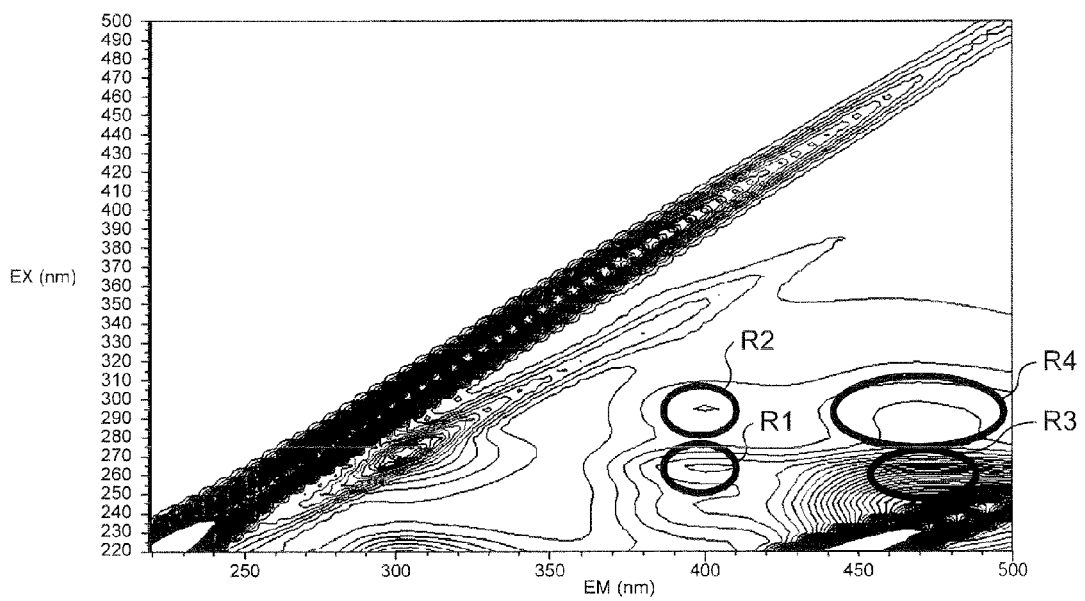
FIG. 1A is a graph illustrating an excitation emission matrix of TFP when adding a TFP solution to sample water with a bromate ion concentration of 0 μg/L and making an acidic condition through the addition of hydrochloric acid.
Figure 1B:
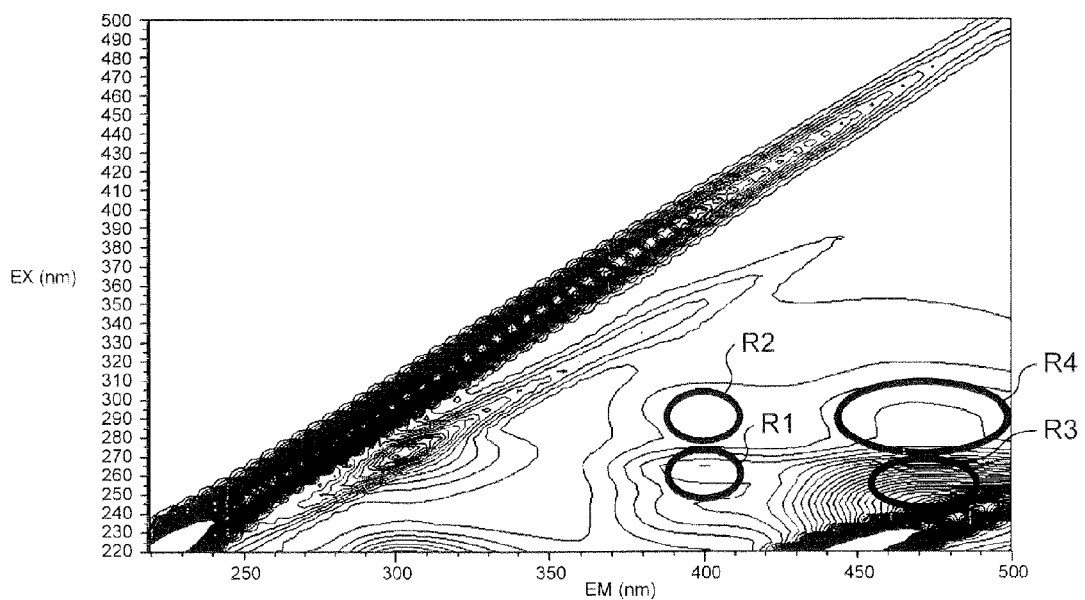
FIG. 1B is a graph illustrating an excitation emission matrix of TFP when adding a TFP solution to sample water with a bromate ion concentration of 20 μg/L and making an acidic condition through the addition of hydrochloric acid.

The inventors of the present invention, as a result of earnest study, have found that the fluorescence intensity of TFP changes also when the excitation wavelength and the emission wavelength are other than 300 nm and 480 nm, respectively. Specifically, FIG. 1A and FIG. 1B are graphs illustrating excitation emission matrix of TFP when adding a TFP solution (294 μM) to two pieces of sample water with a bromate ion concentration of 0 μg/L and 20 μg/L, respectively, and making an acidic condition through the addition of hydrochloric acid. The excitation emission matrix were measured using a spectrofluorophotometer RF-5300PC manufactured by Shimadzu Corporation and a spectrofluorophotometer F-2700 manufactured by Hitachi High-Technologies Corporation.

As is clear from a comparison between FIG. 1A and FIG. 1B, in the presence of bromate ions in the sample water, peaks of the excitation emission matrix were observed when the excitation wavelength and the emission wavelength were 264 nm and 400 nm, respectively (a region R1), when the excitation wavelength and the emission wavelength were 300 nm and 400 nm, respectively (a region R2), when the excitation wavelength and the emission wavelength were 264 nm and 480 cm, respectively (a region R3), and when the excitation wavelength and the emission wavelength were 300 nm and 480 nm, respectively (a region R4).

Figure 2:
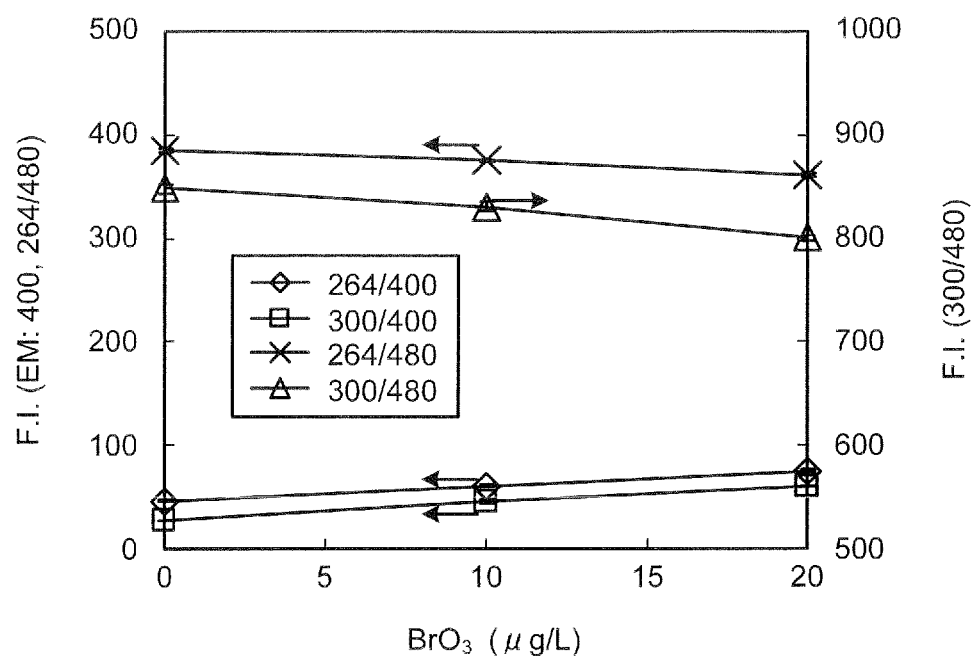
FIG. 2 is a graph illustrating changes in fluorescence intensity (F. I.) with respect to changes in bromate ion concentration at the respective peak wavelengths when the hydrochloric acid concentration is 6 mol/L.

The inventors of the present invention analyzed changes in fluorescence intensity with respect to changes in bromate ion concentration at the excitation wavelengths and the emission wavelengths (hereinafter referred to as "peak wavelengths") at which the peaks of the excitation emission matrix are observed. FIG. 2 is a graph illustrating changes in fluorescence intensity (F. I.) with respect to changes in bromate ion concentration at the respective peak wavelengths. As illustrated in FIG. 2, it was confirmed that when the emission wavelength was 480 nm (the peak wavelengths at the regions R3 and R4), a quenching reaction occurred in which the fluorescence intensity decreased along with an increase in the bromate ion concentration. In contrast, it was confirmed that when the emission wavelength was 400 nm (the peak wavelengths at the regions R1 and R2), a fluorescence reaction occurred in which the fluorescence intensity increased along with an increase in the bromate ion concentration.

Figure 3A:
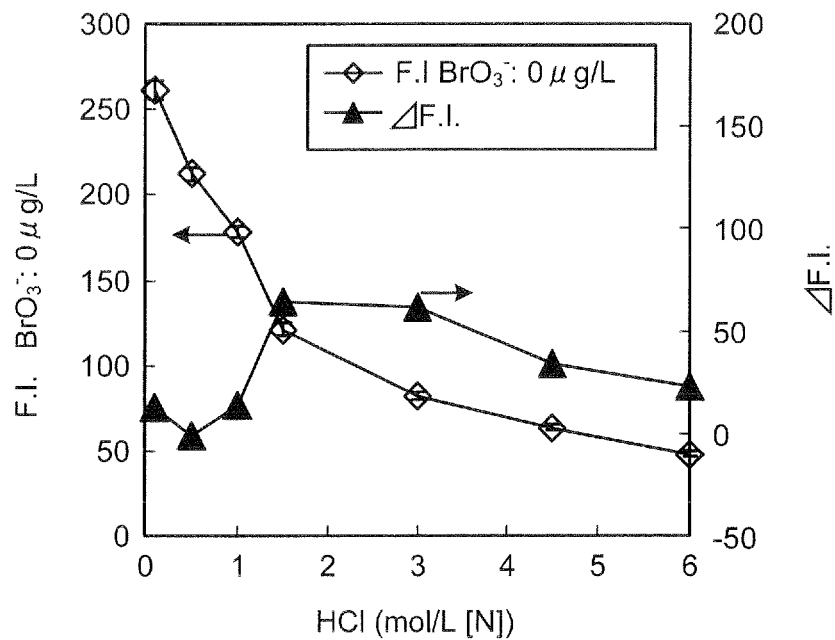
FIG. 3A is a graph illustrating changes in fluorescence intensity (F. I.) when the bromate ion concentration is 0 μg/L and the absolute value of the fluorescence intensity difference (ΔF. I.) between the fluorescence intensity when the bromate ion concentration is 0 μg/L and the fluorescence intensity when the bromate ion concentration is 20 μg/L along with changes in hydrochloric acid concentration when the excitation wavelength and the emission wavelength are 264 nm and 400 nm, respectively.
Figure 3B:
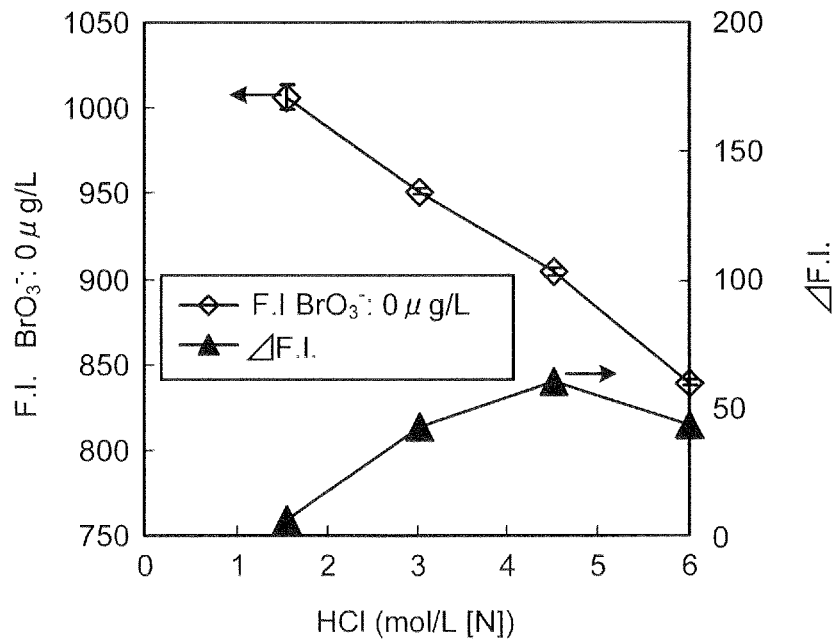
FIG. 3B is a graph for illustrating changes in fluorescence intensity (F. I.) when the bromate ion concentration is 0 μg/l, and the absolute value of the fluorescence intensity difference (ΔF. I.) between the fluorescence intensity when the bromate ion concentration is 0 μg/L and the fluorescence intensity when the bromate ion concentration is 20 μg/L along with changes in hydrochloric acid concentration when the excitation wavelength and the emission wavelength are 300 nm and 480 nm, respectively.

Next, the inventors of the present invention evaluated the optimum hydrochloric concentration when the excitation wavelength and the emission wavelength were 264 nm and 400 nm, respectively, and when the excitation wavelength and the emission wavelength were 300 nm and 480 µm, respectively. FIG. 3A and FIG. 3B are graphs illustrating changes in fluorescence intensity (F. I.) when the bromate ion concentration is 0 µg/L and the absolute value of the fluorescence intensity difference (ΔF. I.) between the fluorescence intensity when the bromate ion concentration is 0 µg/L and the fluorescence intensity when the bromate ion concentration is 20 µg/L along with changes in hydrochloric acid concentration (HCl). FIG. 3A and FIG. 3B illustrate the changes when the excitation wavelength is 264 nm and the emission wavelength is 400 nm, and when the excitation wavelength is 300 nm and the emission wavelength is 480 nm, respectively.

As illustrated in FIG. 3B, when the excitation wavelength and the emission wavelength were 300 nm and 480 nm, respectively, which are the conventional measurement wavelengths, the fluorescence intensity difference with respect to the changes in hydrochloric acid concentration was the maximum and the linearity was also kept within a range of a hydrochloric acid concentration of 4.5 mol/L [N] or more and 6 mol/L [N] or less. Although the optimum hydrochloric acid concentration was within a range of 4.5 mol/L [N] or more and 6 mol/L [N] or less, sufficient reproducibility was not obtained at 4.5 mol/L [N], and it is determined that the optimum hydrochloric acid concentration is 6 mol/L [N] based on reproducibility. As illustrated in FIG. 3A, in contrast, when the excitation wavelength and the emission wavelength were 264 nm and 400 nm, respectively, which are the newly confirmed peak wavelengths, the fluorescence intensity difference with respect to the changes in hydrochloric acid concentration was the maximum and the linearity was kept within a range of a hydrochloric acid concentration of 1.5 mol/L [N] or more and 3 mol/L [N] or less. Although the optimum hydrochloric acid concentration was within a range of 1.5 mol/L [N] or more and 3 mol/L [N] or less, it is determined that the optimum hydrochloric acid concentration is 3 mol/L [N] based on reproducibility.

In view of the foregoing, it has been found that the hydrochloric acid concentration can be reduced to nearly half the conventional hydrochloric acid concentration by setting the excitation wavelength and the emission wavelength to 264 nm and 400 nm, respectively. Although not illustrated, it has been found that both when the excitation wavelength and the emission wavelength are 264 nm and 480 nm, respectively, and when the excitation wavelength and the emission wavelength are 300 nm and 400 nm, respectively, the hydrochloric acid concentration can be reduced similarly. Thus, the hydrochloric acid concentration required for measurement can be reduced by measuring the fluorescence intensity at any time among when the excitation wavelength and the emission wavelength are 264 nm and 400 nm, respectively, when the excitation wavelength and the emission wavelength are 300 nm and 400 nm, respectively, and when the excitation wavelength and the emission wavelength are 264 nm and 480 nm, respectively.

Figure 4:
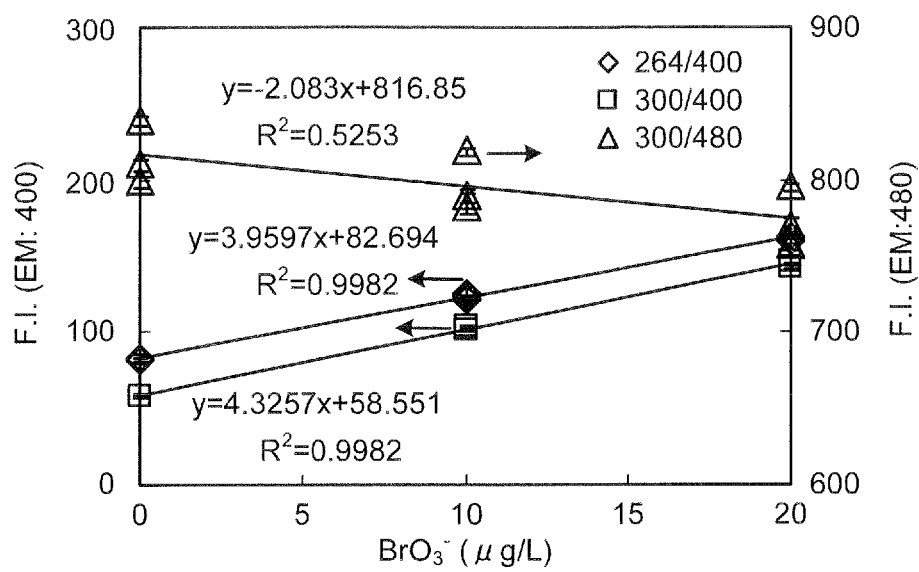
FIG. 4 is a graph illustrating calibration lines between fluorescence intensity (F. I.) and bromate ion concentration determined with respect to the respective peak wavelengths when the hydrochloric acid concentrations are the optimum hydrochloric acid concentrations at the respective peak wavelengths.

FIG. 4 is a graph illustrating results of fluorescence intensity (F. I.) along with changes in bromate ion concentration at the above optimum hydrochloric acid concentrations measured a plurality of times. As illustrated in FIG. 4, when the emission wavelength was 480 nm, the fluorescence intensity varied widely, and the slope of the calibration line varied, but when the emission wavelength was 400 nm, the fluorescence intensity varied little, and the slope did not vary. Although not illustrated, when the fluorescence intensity was measured at room temperature as is the case with a conventional measurement condition with a hydrochloric acid concentration of 3 mol/L [N], no variation or the like in the fluorescence intensity was observed. In view of this, it was determined to measure the fluorescence intensity at the same reaction temperature as the conventional measurement condition.

Figure 5A:
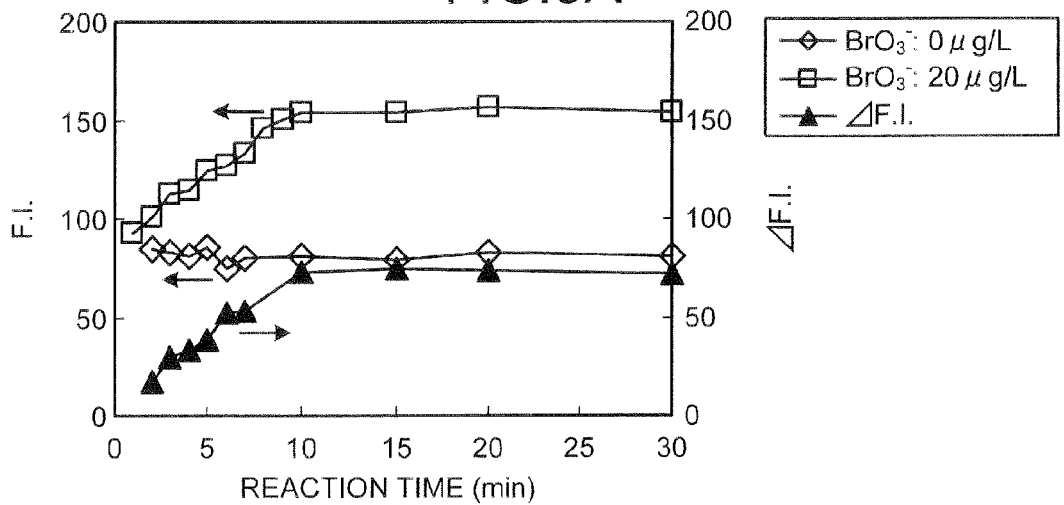
FIG. 5A is a graph illustrating changes in fluorescence intensity (F. I.) for two pieces of sample water whose bromate ion concentrations are 0 μg/L and 20 μg/L, and the absolute value of the fluorescence intensity difference (ΔF. I.) between the fluorescence intensity when the bromate ion concentration is 0 μg/L and the fluorescence intensity when the bromate ion concentration is 20 μg/L with the passage of reaction time when the excitation wavelength and the emission wavelength are 264 nm and 400 nm, respectively.
Figure 5B:
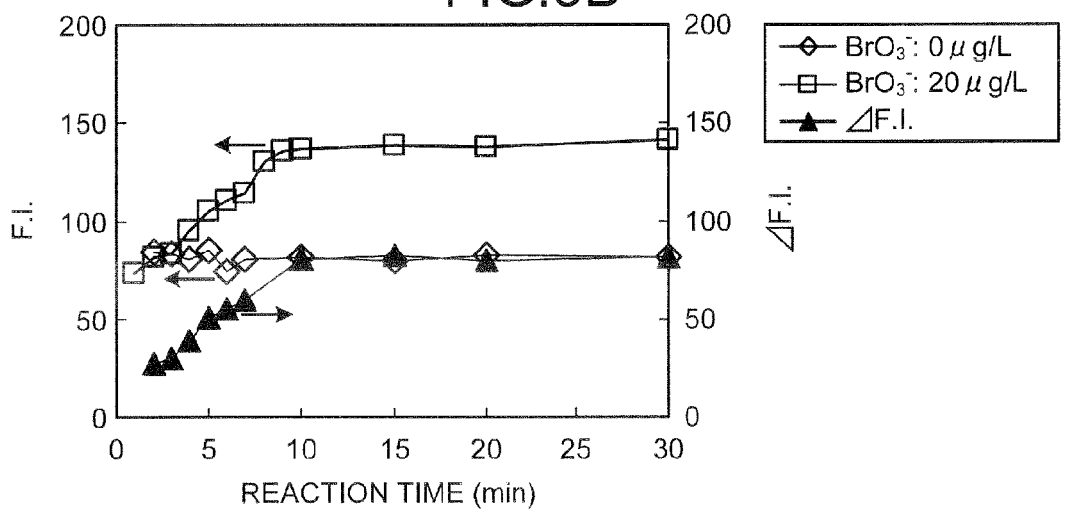
FIG. 5B is a graph illustrating changes in fluorescence intensity (F. I.) for two pieces of sample water whose bromate ion concentrations are 0 μg/L and 20 μg/L, and the absolute value of the fluorescence intensity difference (ΔF. I.) between the fluorescence intensity when the bromate ion concentration is 0 μg/L, and the fluorescence intensity when the bromate ion concentration is 20 μg/L with the passage of reaction time when the excitation wavelength and the emission wavelength are 300 nm and 400 nm, respectively.
Figure 5C:
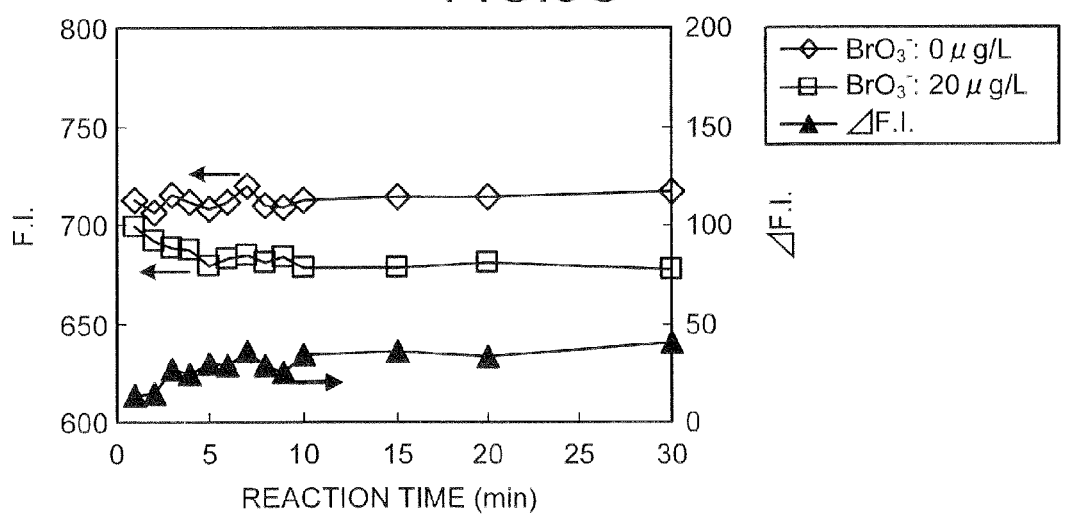
FIG. 5C is a graph illustrating changes in fluorescence intensity (F. I.) for two pieces of sample water whose bromate ion concentrations are 0 μg/L and 20 μg/L, and the absolute value of the fluorescence intensity difference (ΔF. I.) between the fluorescence intensity when the bromate ion concentration is 0 μg/L and the fluorescence intensity when the bromate ion concentration is 20 μg/L, with the passage of reaction time when the excitation wavelength and the emission wavelength are 300 nm and 480 nm, respectively.

FIG. 5A, FIG. 5B, and FIG. 5C are graphs illustrating changes in fluorescence intensity (F. I.) for two pieces of sample water whose bromate ion concentrations are 0 µg/L and 20 µg/L, and the absolute value of the fluorescence intensity difference (ΔF. I.) between the fluorescence intensity when the bromate ion concentration is 0 µg/L and the fluorescence intensity when the bromate ion concentration is 20 µg/L with the passage of reaction time. FIG. 5A, FIG. 5B, and FIG. 5C illustrate the changes when the excitation wavelength is 264 nm and the emission wavelength is 400 nm, when the excitation wavelength is 300 nm and the emission wavelength is 400 nm, and when the excitation wavelength is 300 nm and the emission wavelength is 480 nm, respectively. When the time when hydrochloric acid with a concentration of 3 mol/L [N] was added was set as a reaction time of 0 minute, changes in the fluorescence intensity and the fluorescence intensity difference were measured for the two pieces of sample water whose bromate ion concentration were 0 µg/L and 20 µg/L, with the passage of reaction time at the respective peak wavelengths. It was confirmed that, as illustrated in FIG. 5A, FIG. 5B, and FIG. 5C, the fluorescence intensity differences at the respective peak wavelengths were stabilized after a lapse of 10 minutes. Because of this, it was determined to measure the fluorescence intensity with the same reaction time as the conventional measurement condition.

Figure 6A:
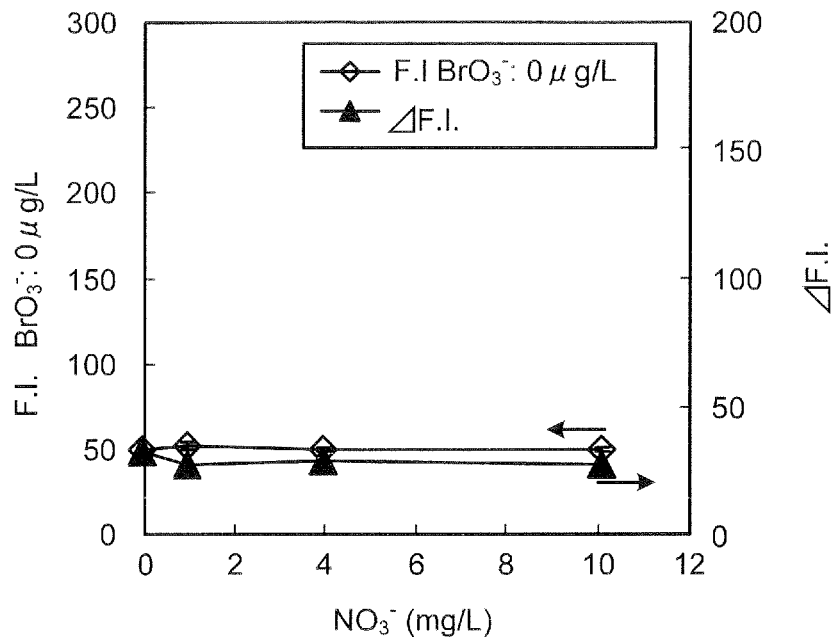
FIG. 6A is a graph illustrating changes in fluorescence intensity (F. I) and the absolute value of the fluorescence intensity difference (ΔF. I.) between the fluorescence intensity when the bromate ion concentration is 0 μg/L and the fluorescence intensity when the bromate ion concentration is 20 μg/L along with changes in nitrate acid concentration when the excitation wavelength and the emission wavelength are 264 nm and 400 nm, respectively.
Figure 6B:
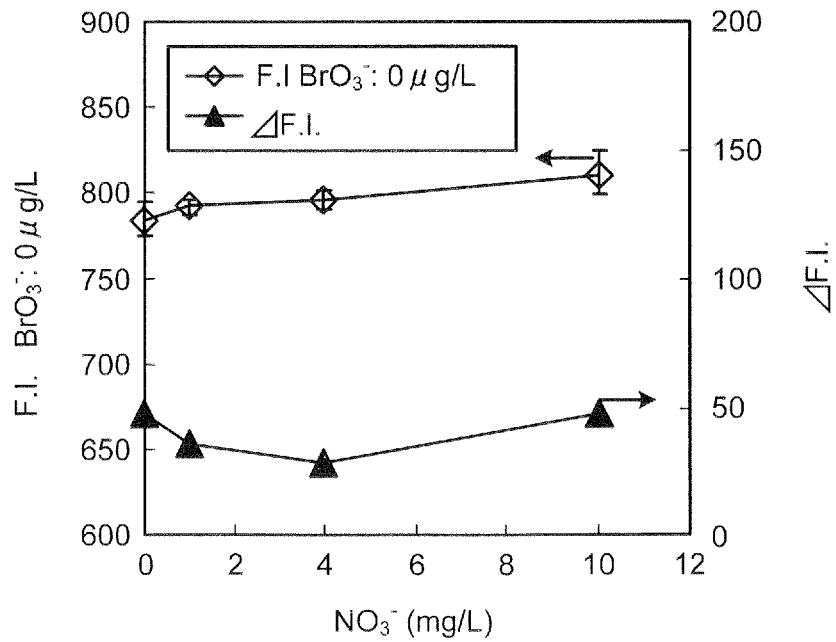
FIG. 6B is a graph illustrating changes in fluorescence intensity (F. I.) and the absolute value of the fluorescence intensity difference (ΔF. I.) between the fluorescence intensity when the bromate ion concentration is 0 μg/L, and the fluorescence intensity when the bromate ion concentration is 20 μg/L along with changes in nitrate acid concentration when the excitation wavelength and the emission wavelength are 300 nm and 480 nm, respectively.

The inventors of the present invention evaluated the influence of nitrate ions on the fluorescence intensity when the excitation wavelength and the emission wavelength were 264 nm and 400 nm, respectively. FIG. 6A and FIG. 6B are graphs illustrating changes in fluorescence intensity (F. I.) when the bromate ion concentration is 0 µg/L, and the absolute value of the fluorescence intensity difference (ΔF. I.) between the fluorescence intensity when the bromate ion concentration is 0 µg/L and the fluorescence intensity when the bromate ion concentration is 20 µg/L along with changes in nitrate ion concentration ($NO_3^-$). FIGS. 6A and 6B illustrate the changes when the excitation wavelength is 264 nm and the emission wavelength is 400 nm, and when the excitation wavelength is 300 nm and the emission wavelength is 480 nm, respectively. As illustrated in FIG. 6B, when the excitation wavelength and the emission wavelength were 300 nm and 480 nm, respectively, which are the conventional measurement wavelengths, it was hard to calculate the bromate ion concentration accurately because the fluorescence intensity varied widely along with the changes in nitrate ion concentration, and the slope of the intensity changes varied. As illustrated in FIG. 6A, in contrast, when the excitation wavelength and the emission wavelength were 264 nm and 400 nm, which are the newly confirmed peak wavelengths, the bromate ion concentration can be calculated accurately because the fluorescence intensity changed little along with the changes in nitrate ion concentration, and the slope did not vary. In view of this, it has been found that the bromate ion concentration can be measured with high precision without being affected by the nitrate ions by setting the excitation wavelength and the emission wavelength to 264 nm and 400 nm, respectively. Although not illustrated, it has been found that also when the excitation wavelength and the emission wavelength were 300 nm and 400 nm, respectively, the bromate ion concentration can be measured with high precision without being affected by the nitrate ions.

Figure 7:
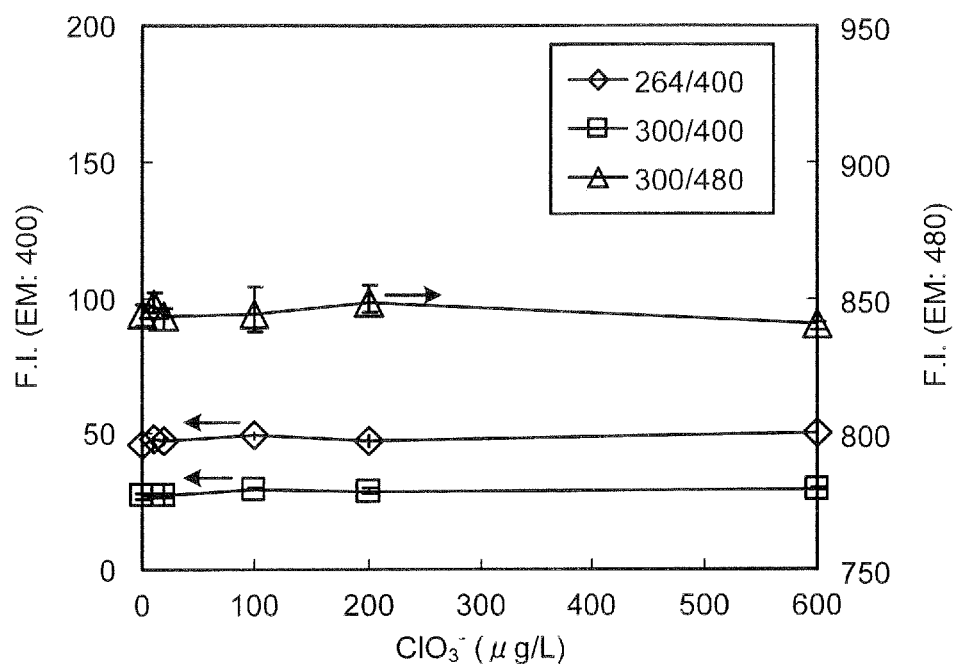
FIG. 7 is a graph illustrating changes in fluorescence intensity (F. I.) when the bromate ion concentration is 0 μg/L with respect to changes in the concentration of chlorate ions at the respective peak wavelengths.

When performing ozonation on raw water, if the raw water contains free chloride, the free chloride affects the measurement accuracy of fluorescence intensity. If the raw water contains free chloride, ozonation produces chlorate ions ($ClO_3^-$). The inventors of the present invention measured changes in fluorescence intensity with respect to changes in the concentration of chlorate ions at the respective peak wavelengths for a solution with a bromate ion concentration of 0 µg/L. FIG. 7 is a graph illustrating changes in fluorescence intensity (F. I.) when the bromate ion concentration is 0 µg/L with respect to changes in the concentration of chlorate ions at the respective peak wavelengths. As illustrated in FIG. 7, the fluorescence intensity at the respective peak wavelengths did not change significantly even when the concentration of chlorate ions changed. Based on this, it has been confirmed that chlorate ions are not an interfering substance on accurate measurement of fluorescence intensity.

As is clear from the foregoing description, the method for measuring bromate ions as one embodiment of the present invention includes: a first step of adding a fluorescent substance whose fluorescence intensity changes through coexistence with bromate ions to sample water and making an acidic condition through the addition of hydrochloric acid; a second step of measuring the fluorescence intensity of the fluorescent substance; a third step of calculating the difference between the fluorescence intensity of reference sample water that contains no bromate ion and the measured fluorescence intensity as a fluorescence intensity difference; and a fourth step of calculating bromate ion concentration from the calculated fluorescence intensity difference using a pre-determined calibration line between fluorescence intensity difference and bromate ion concentration. In the method, the second step includes a step of measuring the fluorescence intensity at any time among when the excitation wavelength and the emission wavelength are 264 nm and 400 nm, respectively, when the excitation wavelength and the emission wavelength are 264 nm and 480 nm, respectively, and when the excitation wavelength and the emission wavelength are 300 nm and 400 nm, respectively, thereby measuring the bromate ion concentration with high precision while reducing the hydrochloric acid concentration required for measurement.

Although the present invention has been described using an embodiment, it is needless to say that the technical scope of the present invention is not limited to the embodiment. It is clear for those skilled in the art that various alterations or improvements can be made to the embodiment. It is clear from the recitation of the claims that embodiments to which the various alterations or improvements are made are also included in the technical scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for measuring bromate ions, the method comprising:
    an adding step of adding a fluorescent substance whose fluorescence intensity changes by coexistence of bromate ions to sample water and further adding hydrochloric acid to a sample mixture of the sample water with the fluorescence substance so that the sample mixture becomes an acidic condition;
    a measuring step of measuring the fluorescence intensity of the fluorescent substance;
    a difference calculating step of calculating a difference between the fluorescence intensity measured at the measuring step and a reference fluorescence intensity of reference sample water that contains no bromate ion as a fluorescence intensity difference; and
    a concentration calculating step of calculating bromate ion concentration from the fluorescence intensity difference calculated at the difference calculating step using a pre-determined calibration line between fluorescence intensity difference and bromate ion concentration, wherein
    the measuring step includes a step of measuring the fluorescence intensity at any one of cases where,
    (a) an excitation wavelength is 264 nm and an emission wavelength is 400 nm,
    (b) the excitation wavelength is 264 nm and the emission wavelength is 480 nm, and
    (c) the excitation wavelength is 300 nm and the emission wavelength is 400 nm.

2. An apparatus for measuring bromate ions, comprising:
    an adding unit that adds a fluorescent substance whose fluorescence intensity changes by coexistence of bromate ions to sample water and further adds hydrochloric acid to a sample mixture of the sample water with the fluorescence substance so that the sample mixture becomes an acidic condition;
    a measuring unit that measures the fluorescence intensity of the fluorescent substance;
    a difference calculating unit that calculates a difference between the fluorescence intensity measured by the measuring unit and a reference fluorescence intensity of reference sample water that contains no bromate ion as a fluorescence intensity difference; and
    a concentration calculating unit that calculates bromate ion concentration from the fluorescence intensity difference calculated by the difference calculating unit using a pre-determined calibration line between fluorescence intensity difference and bromate ion concentration, wherein
    the measuring unit that measures the fluorescence intensity measures the fluorescence intensity at any one of cases where,
    (a) an excitation wavelength is 264 cm and an emission wavelength is 400 nm,
    (b) the excitation wavelength is 264 nm and the emission wavelength is 480 nm, and
    (c) the excitation wavelength is 300 nm and the emission wavelength is 400 nm.

* * * * *